United States Patent
Berlowitz-Tarrant et al.

[11] Patent Number: 5,840,387
[45] Date of Patent: Nov. 24, 1998

[54] SULFONATED MULTIBLOCK COPOLYMER AND USES THEREFOR

[75] Inventors: Laurence Berlowitz-Tarrant, Harvard, Mass.; Timothy N. Tangredi, Palm Harbor, Fla.; Gary E. Wnek, Latham, N.Y.; Robert J. Nicolosi, Tyngsboro, Mass.

[73] Assignee: Aegis Biosciences L.L.C., Palm Harbor, Fla.

[21] Appl. No.: 661,111

[22] Filed: Jun. 10, 1996

Related U.S. Application Data

[60] Provisional application No. 60/001,973, Jul. 28, 1995.
[51] Int. Cl.$^6$ ..................................................... B29D 22/00
[52] U.S. Cl. ................. 428/36.91; 428/36.9; 428/36.92; 424/400; 424/78.31; 424/422; 424/239; 604/239; 623/1; 623/2; 623/3; 623/12; 623/900
[58] Field of Search .............................. 424/400, 78.31, 424/422; 604/239; 623/1, 2, 3, 12, 900; 428/36.9, 36.91, 36.92

[56] References Cited

U.S. PATENT DOCUMENTS

| | | | |
|---|---|---|---|
| 3,925,280 | 12/1975 | Lundberg et al. | 260/23 |
| 5,239,010 | 8/1993 | Balas et al. | 525/314 |
| 5,296,235 | 3/1994 | Sawayanagi et al. | 424/486 |
| 5,389,092 | 2/1995 | Guillemet et al. | 604/304 |
| 5,407,715 | 4/1995 | Buddenhagen et al. | 428/35.7 |
| 5,468,574 | 11/1995 | Ehrenberg et al. | 429/33 |

FOREIGN PATENT DOCUMENTS

| | | |
|---|---|---|
| 58-203766 | 11/1983 | Japan . |
| 4-208165 | 7/1992 | Japan . |
| 4-210640 | 7/1992 | Japan . |
| 8-43377 | 2/1996 | Japan . |

OTHER PUBLICATIONS

Annekova et al., "Synthetic Polymeric Blood Anticoagulants of Direct Action", *Khimiko–Farmatsevticheskii Zhurnal*, vol. 16, Dec. 1980, pp. 93–96.

Kammangne, F.M., "Heparin–like Activity of Insoluble Sulphonated Polystyrene Resins", *Biomaterials (England)*, vol. 6, No. 5, pp. 297–302. (1985).

*Primary Examiner*—S. Mark Clardy
*Assistant Examiner*—Michael A. Williamson
*Attorney, Agent, or Firm*—Giulio A. DeConti, Jr.; Mark D. Russett; Lahive & Cockfield, LLP

[57] ABSTRACT

Sulfonated multiblock copolymers, and uses thereof, are disclosed. The sulfonated copolymers are useful for providing non-thrombogenic coatings, e.g., for medical devices, and for promoting cell growth, differentiation, or production of normal cell products. The sulfonated copolymers are also useful for administration of therapeutic agents.

19 Claims, 3 Drawing Sheets

SULFONATED MULTIBLOCK COPOLYMER AND USES THEREFOR

RELATED APPLICATIONS

This application claims benefit of priority under 35 U.S.C. 119(e) to U.S. Provisional application Ser. No. 60/001,973, filed Jul. 28, 1995, the contents of which is hereby incorporated by reference.

BACKGROUND OF THE INVENTION

The need for biocompatible materials for use in medical applications is acute. Many materials used for medical devices are selected for mechanical strength or stability in the body, but are capable of causing thrombogenesis and other undesirable side effects when in contact with blood or blood products. Prior art approaches to preventing thrombogenesis include the covalent or non-covalent attachment of non-thrombogenic molecules to the surface of an implantable device. For example, heparin has been attached to the surface of implantable materials in an effort to reduce thrombogenicity of the material (see, e.g., U.S. Pat. No. 3,826,678; 4,526,714; 4,613,517; 5,061,750).

However, this approach has the disadvantage of providing a coating on the surface of the material only; thus, if the surface coating is abraded or washed off, the thrombogenic material will be exposed, possibly resulting in clot formation. Also, recent studies have concluded that heparinized surfaces are only modestly effective at preventing adverse outcomes in patients.

In addition to the need for biocompatibility of materials, it is now generally recognized that there is a further need for bioactive materials, that is, materials that can stimulate or promote normal tissue functions such as conduction, growth and differentiation of cells, and the production of materials characteristic of normal cellular activity. For example, endothelial cells should be attracted (i.e., conducted) to the surface of an implanted material. Cells attracted to the material surface should also produce the products typically expressed by normal cells; for example, endothelial cells should produce natural clot inhibitors.

SUMMARY OF THE INVENTION

This invention pertains to methods of using an anionic multiblock copolymer which is biocompatible and which has desirable properties such as nonthrombogenicity. The anionic multiblock copolymer can also be used to deliver drugs, or to promote endothelialization or epithelialization, and other forms of conduction, growth, or differentiation of cells and tissues. In one aspect, the invention features a nonthrombogenic article for use in contact with blood or blood products, the article having at least one surface, the surface comprising an anionic multiblock copolymer. In a preferred embodiment, the multiblock copolymer is a sulfonated styrene-ethylene/butylene-styrene triblock copolymer. In preferred embodiments, the multiblock copolymer is at least 20%, 30%, 50%, 70% or 90% sulfonated. In preferred embodiments, the nonthrombogenic article is a medical device. In preferred embodiments, the article comprises a hybrid material comprising a triblock copolymer and a material selected from the group consisting of Teflon®, Dacron®, titanium oxide, magnetic particles, and calcium phosphate. In preferred embodiments, the article is selected from the group consisting of stents, catheters, cannulae, tubing, vascular grafts, artificial hearts, heart valves, pacemakers, implants, artificial joints, and prostheses. In a preferred embodiments, the article is an electrical lead, e.g., for an implanted medical device.

In another aspect, the invention features a method of manufacturing a thromboresistant article, the method comprising coating at least one surface of an article with an anionic multiblock copolymer.

In still another aspect, the invention features a method of promoting cell growth, or adhesion, comprising contacting cells with an anionic multiblock copolymer, under conditions such that cell growth, differentiation, or production of normal cell products is promoted. In preferred embodiments, the cell are endothelial cells, epithelial cells, osteoblasts, or islet cells.

In yet another aspect, the invention provides a method of administering a therapeutic agent to a subject, the method comprising contacting the subject with an anionic multiblock copolymer, wherein the copolymer entraps the therapeutic agent, such that the therapeutic agent is delivered to said subject.

In another aspect, the invention provides a medical implant which can be modified in situ by application of an electric field. In this aspect, the implant comprises an anionic multiblock copolymer, preferably a sulfonated styrene-ethylene/butylene-styrene triblock copolymer.

DETAILED DESCRIPTION OF THE INVENTION

The present invention features methods of using an anionic copolymer. In one aspect, the invention provides a method of manufacturing a thromboresistant article. The method comprises coating at least one surface of an article with an anionic multiblock copolymer. A thromboresistant article can also be fabricated entirely from an anionic multiblock copolymer. The term "block copolymer" is known in the art, and refers to a copolymer of two or more monomers in which the polymeric chains contain long stretches (e.g., at least about 10 monomer units on average) of one kind of repeating unit linked covalently to one or more long stretches of repeating units of one or more different polymers. For example, a block copolymer of components A and B could have a partial structure $(A)_n(B)_m(A)_p$, where n, m, and p are, independently, integers which are generally greater than 10 on average, and are each preferably, on average, in the range between 5 and 1000, more preferably between 10 and 100. Preferred copolymers include multiblock (i.e., diblock, triblock, and the like) copolymers composed of hydrocarbon subunits (prior to sulfonation). For example, preferred blocks include styrene, ethylene/butylene, isoprene, butadiene, propylene, and the like. Preferred sulfonated copolymers are not sulfonated in all blocks (e.g., only styrene is sulfonated). A particularly preferred copolymer is styrene-ethylene/butylene-styrene, which is available from Shell Chemical. This copolymer can be sulfonated by methods known in the art. A suitable sulfonation method is described in U.S. Pat. No. 5,468,574 to Ehrenberg et al. This patent teaches, inter alia, the use of sulfur trioxide and triethyl phosphate in dichloroethane/cyclohexane solution for the sulfonation of styrene-ethylenelbutylene-styrene. Sulfonation according to this method sulfonates principally the styrene blocks. The copolymer can be sulfonated to a desired extent by controlling the sulfonation conditions; alternatively, the monomer units (e.g., the styrene monomer) can be separately sulfonated and then combined with the remaining monomer units and copolymerized. The skilled artisan will appreciate that the block lengths and other characteristics of the copolymer can be varied by changing the polymerization conditions; thus, it is possible to alter the copolymer morphology (e.g., microphase separation) and the bulk physical properties of the copolymer. Other copolymers can also be used in the methods of the invention, as taught in the above-referenced U.S. Pat. No. 5,468,574.

Although reference is made herein to sulfonated copolymers, other anionic copolymers may be used in the methods of the present invention. Thus, while copolymers with sulfonate functional groups are particularly preferred, copolymers comprising other anionic moieties such as sulfates, phosphates, phosphonates, carboxylates, phenolates and the like, or mixtures thereof, may be useful according to the present invention. More than one type of anionic moiety group may be employed in a particular copolymer. Such copolymers are known in the art and/or can be made according to known techniques.

The sulfonated copolymers of the invention can be molded, cast, laminated, extruded, worked or shaped to provide a variety of useful forms, according to standard techniques for forming polymers. For example, the subject copolymers can be cast by dissolving the copolymer in a suitable solvent (for example, n-propanol and dichloroethane), casting the mixture into a form, and removing the solvent to yield the cast product, according to standard techniques. In a preferred embodiment, after casting, an IR lamp is used to dry and cure the copolymer.

The copolymers of the invention can also be used as a coating to cover a substrate. Exemplary substrates include metals, ceramics, and polymers (natural or synthetic). In addition, the sulfonated styrene-ethylene/butylene-styrene copolymer can be effectively grafted to a variety of ceramic and polymer substrates, including polyvinyl polymers (such as polyvinylchloride and polyethylene), mylar and the like. Non-polymeric substrates can be employed by appropriate surface modification to facilitate grafting. Grafting can be by a variety of well-known techniques, including the use of corona discharge, UV irradiation, ionizing radiation, plasmas, and the like. The copolymers of the invention may be used to form the surface of a wide variety of medical devices, as described below.

The sulfonated copolymer of the invention can also form hybrid materials with polymers or ceramic materials, thus combining the physical or chemical properties of those materials with the biological, chemical, and controlled-release characteristics of the copolymer, to create novel hybrids. Where the anionic copolymer is substantially soluble in organic solutions, porous structures are readily infiltrated. Exemplary materials which can be infiltrated in this manner are: glass fiber mat; porous Teflon® (tetrafluoroethylene) and Dacron® (polyethylene terephthalate), e.g., as currently used in vascular grafts; porous or pitted native titanium oxide and sintered and non-sintered calcium phosphate, e.g., as used in coatings of dental and orthopedic implant devices. By controlling the amount of polymer applied to a surface it is possible to only partially cover pore surfaces, thus producing a desired net porosity.

Another method of hybrid formation consists in particles of another material being suspended in the dissolved or suspended sulfonated copolymer of the invention, the particles remaining suspended in the sulfonated copolymer solution or suspension. Alternatively, the inorganic material can be synthesized in situ, using, e.g., a sol-gel approach, to create a fine dispersion of the particles. As an extension of this method, it is possible to prepare the particulate material in the sulfonated domains of the sulfonated copolymer of this invention after casting the sulfonated copolymer into a film, for example, by using the sol-gel approach described above. The particulate material can be e.g., a polymer, ceramic, or metallic powder. The particle size can range, e.g., from about 100 nanometers to about 1000 microns in diameter, more preferably from about 10 microns to about 100 microns in diameter. One illustrative hybrid formed in this manner is a hybrid of the sulfonated copolymer and suspended magnetic particles, metals, or metal oxides, with or without organic derivatization. Such a hybrid can be used, e.g., to coat orthopedic or dental implants. A magnetic field induced in this hybrid can improve bone healing in ways well-known in the art.

In another aspect, the invention features a nonthrombogenic article for use in contact with blood or blood products, the article comprising at least one surface, said surface comprising a sulfonated multiblock copolymer. Articles, e.g., medical devices, for which the copolymer can form a surface include stents, catheters, cannulae, tubing (e.g., for use in kidney dialysis and heart-lung machines), vascular grafts, artificial hearts, heart valves, venous valves, pacemakers (including leads for pacemakers), implantable defibrillators, implants (for example, implants to be placed in bone), artificial joints, prostheses, and the like. Such medical devices have significant advantages over current devices, e.g., cardiovascular devices which are thrombogenic and non-endothelializing, or implants to be placed in bone which induce encapsulation with fibrous connective tissue, rather than with bone. For example, stents are often placed after balloon angioplasty to prevent restenosis of the blood vessel. The placement of the stents requires the use of clotting inhibitors for several weeks before and after angioplasty, resulting in long hospital stays, considerable expense and risk to the patient. Placement of a nonthrombogenic stent prepared according to the method of the present invention would reduce or eliminate the need for additional antithrombogenic measures.

The subject sulfonated copolymers have several properties which make them valuable for use in medical devices. As described in Example 1, infra, the sulfonated copolymers possess antithrombogenic properties. The ability to prevent thrombogenesis makes the subject sulfonated copolymers useful in applications which require contact with blood or blood products. The copolymers have several advantages over coatings known in the art. For instance, a device composed of one of the subject copolymers is inherently antithrombogenic, that is, there is no antithrombogenic surface coating which can wash off or be abraded or degraded. Thus, the antithrombogenic properties of such a device are substantially permanent rather than temporary. Such properties is desirable in a permanently implanted device.

Furthermore, the magnitude of the antithrombogenic quality of the subject copolymers can be controlled by controlling the degree of sulfonation of the copolymer. As described in Example 1, increasing the degree of sulfonation from 30% to 74% more than doubles the time required for blood to clot. Thus, a copolymer having a predetermined degree of sulfonation can be used to ensure a desired antithrombogenic effect of the copolymer. In preferred embodiments, the sulfonated triblock copolymer is at least 20%, 30%, 50%, 70% or 90% sulfonated. Sulfonation is expressed as a percentage of available styrene units which are sulfonated.

In another aspect of the invention, sulfonated multiblock copolymers can be used as promoters of endothelialization or epithelialization. It is well known that anionic glycosaminoglycans (GAGs) are associated with cell membrane or extracellular matrix (ECM), and that the growth (and, under certain conditions, differentiation and cell-type-specific functions) of cells is promoted by GAGs. The anionic nature of the subject sulfonated copolymers is analogous to GAGs; thus, articles which have a surface comprising the subject copolymers can promote cell growth, binding of the cells to the material, cell differentiation, and production of normal cell- or tissue-specific products. Accordingly, in one aspect, the invention features a method of promoting cell growth or adhesion. The method includes the step of contacting cells with a sulfonated multiblock copolymer, under conditions such that cell growth or adhesion is promoted.

Endothelialization is the growth of endothelial cells on a surface. The endothelium, or lining of the blood vessels and the heart, has a vital role in resisting clotting and generally maintaining the integrity of the cardiovascular organs. One of the functions of endothelial cells is to produce anticlotting factors. Implantation of a device into the blood vessels or the heart can cause foreign body responses, which can result in eventual organ failure, as well as clots produced by the disruption of normal circulation dynamics by the device. If a layer of endothelium could be induced to grow over the device, the implant would effectively cease to present a foreign surface to the bloodstream, and these problems would be reduced or eliminated. We have found that aortic endothelial cells are conducted or attracted to a sulfonated copolymer surface and grow in an in vitro tissue culture system (data not shown). Furthermore, the growing cells were assayed by an enzyme immunoassay (EIA) and were found to produce prostacyclin, a product of normal endothelium. Thus, in a preferred embodiment, the invention provides a method of promoting endothelialization or epithelialization. Such a method is valuable both for promoting the conduction and growth of epithelial or endothelial cells in vivo (for example, on an implant or other medical device), and in vitro (for example, to grow cells for use in grafting, e.g., skin grafts). Growth and conduction of other types of healthy cells, including osteoblasts, odontoblasts, chondrocytes, and other connective tissue cells, as well as their induction or differentiation from precursor cells, can also be promoted in a similar fashion. For example, the integration of a bone implant into a bone can be improved by use of a sulfonated copolymer surface on the implant, such that osteoblast conduction, differentiation, and growth on and around the implant is promoted. In periodontal disease, the ability of the gingival epithelium to grow on the surface of the material makes it useful in promoting bone and ligament healing in periodontal disease.

In still another aspect, the invention provides methods of administering a therapeutic agent to a subject, i.e., controlled release. Polymers are useful as drug carriers for controlled release. Up to 5 years of relatively steady release has been achieved (the Norplant birth control implant system is an example). A first type of drug-release system is said to be 'diffusional' since simple diffusion of the drug through the polymer is the release mechanism. In such a system, the polymer generally does not significantly dissolve or degrade and, if implanted, must be surgically removed after the drug has been delivered. Such controlled release materials are particularly suitable as permanent coatings on non-resorbed, implanted devices, such as tooth implants and cardiovascular stents.

Another type of polymeric drug release devices involves bioerodible polymers, where the polymer matrix erodes with time ('erosional') to non-toxic products which can be metabolized or eliminated, circumventing the need to surgically remove the polymer after release is complete.

More recently, attention has focused on a third generation type of drug-release system. Development of these systems is driven by the recognition that in certain biomedical applications, continuous, low-level release may not be desirable. For example, for delivery of hormones such as insulin, pulsed release at specific times is desirable.

In a preferred embodiment, the method comprises contacting the subject with a sulfonated multiblock copolymer, wherein the copolymer entraps a therapeutic agent, such that the therapeutic agent is delivered to the subject. It is believed that at least some of the subject sulfonated multiblock copolymers are hydrogels; thus, the copolymers can be made to entrap (or immobilize), and subsequently release, a variety of therapeutic agents. Data from microscopy and x-ray scattering experiments show that a film formed from a sulfonated styrene-ethylene-butylene-styrene block copolymer has a lamellar morphology where the sulfonated PS (polystyrene) and EB (ethylene/butylene) phases form alternating plates or layers with thicknesses of about 200–300 Å. The high ionic conductivities observed in polymer films of sulfonated styrene-ethylene-butylene-styrene block copolymer suggest that sulfonated PS 'sheets' extend through the thickness of the membrane. As with certain known block copolymers, there are distinct phases due to poor molecular compatibility (e.g., hydrophobicity/hydrophilicity) of the components, along with a thin interphase region at or near the block junctions where there is at least some small degree of mixing. As a result, there are least three locations for added molecules to reside in the film: largely in the EB phase if they are very non-polar or hydrophobic; largely in the S-PS (sulfonated polystyrene) phase if they are very hydrophilic; and at the interphase if the added molecule is, e.g., cationic with at least some hydrophobic character (e.g., a cationic surfactant). Another possible location for a guest molecule occurs within the S-PS domain near a block region having a sulfonated styrene flanked by unsulfonated styrenes, the latter being hydrophobic. For these reasons many types of molecular species can be trapped and immobilized in, or released from, the copolymeric matrix.

In a preferred embodiment, the therapeutic agent is entrapped by including the guest, e.g., therapeutic, agent in the casting solvent when the copolymer is cast, or coated onto a substrate. In this way, the therapeutic agent is distributed throughout, and is integral with, the copolymer structure. Examples of therapeutic agents include enzymes (for example, glucose oxidase or lumbrikinase, a fibrinolytic enzyme), antiinflammatories, analgesics, growth factors, antibiotics, steroids, hormones, antiviral agents, neurotransmifters or neuroregulators, antibodies, antiplatelet agents (such as carbamoylpiperidines) and the like. In another embodiment, the therapeutic agent is immobilized or associated with the sulfonated copolymer by adsorption or through ionic (e.g., electrostatic) interactions. For example, neuroregulators such as dopamine are cationic and bind well to the subject copolymer. Since dopamine deficiency is linked to Parkinson's disease, an article comprising a sulfonated copolymer film that includes dopamine can be implanted in the brain to offer sustained doses of the neuroregulator.

Figure 1A:
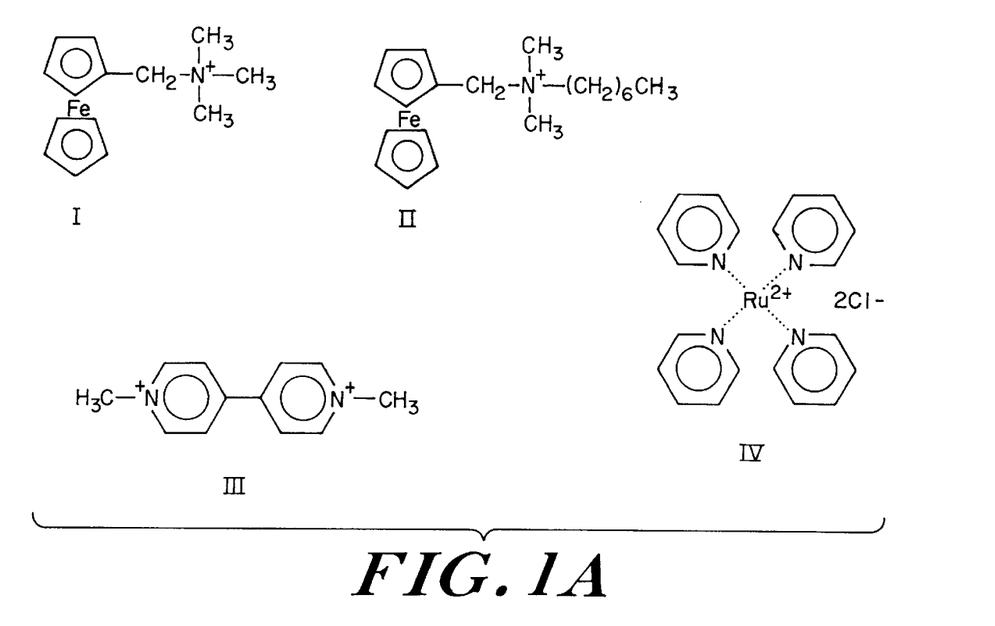
FIGS. 1A and 1B show the chemical structures of several molecules which have been immobilized in a sulfonated triblock copolymer.

In certain embodiments, the therapeutic agent is primarily immobilized on the surface of the copolymer, while in other embodiments, the therapeutic agent is distributed throughout the copolymer structure. For example, the anionic nature of the sulfonated copolymers permits the immobilization of cationic species through ionic interactions. Thus, cationic species such as amines, amino acids, basic proteins, and the like can be immobilized on the copolymer surface or in the copolymer structure. It is believed that polycations are generally immobilized on the surface, whereas smaller cations are often found throughout the copolymer. For example, compound I (FIG. IA) is bound to about 80% of the sulfonate groups in a sulfonated copolymer film. Moreover, non-cationic species can be derivatized to yield a cationic derivative. For example, a non-cationic protein can be made cationic by conversion of carboxylates (Glu and Asp) to amines with ethylenediamine, or by addition of a polylysine "tail" to the protein. Other compounds can similarly be modified to provide cationic derivatives by methods known in the art.

For diffusional release, the rate of release is determined, at least in part, by how strongly the drug is bound to polymer. There are several ways to control the rate of release. In a preferred embodiment, the sulfonation level of the subject copolymer is modified. Lower sulfonation increases the hydrophobicity of the sulfonated polystyrene (S-PS) phase and can lead to stronger binding of a hydrophobic, positively-charged drug. Also, the degree of swelling of the polymer is generally lower at lower sulfonation, making drug diffusion slower. It will be apparent to the skilled artisan that drugs can be selected or modified to obtain a desired (e.g., preselected) rate of release from a selected copolymer.

Other methods of controlling the rate of diffusional release can also be employed. For example, in the method described above, S-PS lamellae can function, at least in part, as cation-exchange regions, where as a cationic drug is released, cations such as $Na^+$ or $K^+$ (e.g., from the serum) diffuse into the polymer to replace the released drug. In an alternative embodiment, the counter-ion for the S-PS phase can be a "modifier cation," such as a quaternary ammonium surfactant, which is tightly bound and not released from the polymer. The function of the "modifier cation" is to "tune" or adjust the hydrophilic/hydrophobic balance in the copolymeric lamellae for binding of various drugs which are not readily released from the native copolymer, in which a typical counter-ion is $Na^+$. A partial exchange (e.g., 10–20%) of native $Na^+$ with a modifier cation, followed by exchange of the remaining $Na^+$ with a cationic drug, can produce a release rate considerably modified from the release rate of the native copolymer, permitting a fine-tuned rate of release.

While a therapeutic agent can be released by diffusion, solubilization, and the like, it is also possible to cause release of an agent by applying an electric field to the copolymer entrapping the drug. The electric field can be weak, preferably in the range of 5–20 volts/cm. Modulation can be controlled by the hydrophobicity of molecular species lining the S-PS lamellae (as described above) and by controlling redox reactions that fine-tune the ionic conductivity (see, e.g., Example Three below). Thus the sulfonated copolymer can be used as a material for pulsatile release, in which periodic releases of a therapeutic agent can be controlled by application of pulses of electric current to the copolymer. In this way the sulfonated copolymer can be used as a field-stimulated gate, releasing chemicals on demand.

Yet another method for controlling release derives from the electrostatic qualities of the inventive membrane. Ferrofluids (available from, e.g., Ferrofluidics Inc.) are single-domain magnetic particles (ca. 100 Å in diameter) that have organic surface functionality. Immersing the polymer film in a solution of a cationic ferrofluid leads to electrostatic attachment of the magnetic particles to surface sulfonates, rendering the membrane deformable in a magnetic field. By oscillating a magnet field near the film, a rapid sinusoidal deflection of the polymer can produce pulsatile release.

Furthermore, it is possible to immobilize compounds by "layering" materials on the sulfonated copolymer surface. For example, a polycation, such as polylysine, can be immobilized on the anionic copolymer surface, as described above. A polyanionic material, such as chondroitan sulfate, can then be immobilized to the polycation layer. In this fashion, a hydrophobic charged environment can be created which is similar to ECM. Such an environment could be used to promote the growth of islets cells, osteoblasts, and the like. Artificial organs, such as an artificial pancreas, can therefore be made according to the present invention. The sulfonated multiblock copolymer also functions as a size-exclusion membrane, and therefore could allow oxygen and nutrients to reach the cells, and insulin to pass out of the artificial organ, when implanted in vivo. In addition, the surface ionic charge density can be increased by "layering", e.g., by first binding a polycation, such as poly(lysine), to a lightly sulfonated surface, and then binding a more heavily sulfonated polymer, e.g., sulfonated polystyrene, to the polycation layer.

In another preferred embodiment, the polyanion is a nucleic acid. In this embodiment, the invention provides a method of administering a nucleic acid construct to a cell, by contacting a cell with a nucleic acid construct immobilized on a polycationic surface which is, immobilized on a sulfonated copolymer. Gene therapy by delivery of nucleic acid/polycation complexes to cells is well known (see, e.g., U.S. Pat. No. 5,166,320 to Wu).

It will be appreciated that the mode of immobilization of the therapeutic agent will be selected to ensure desirable characteristics of the resulting copolymer. For example, the skilled artisan will be able to incorporate the therapeutic agent in an amount or concentration sufficient to ensure that a therapeutically effective amount of the agent will be released to the subject when the copolymer is implanted into (or otherwise contacted with) the subject. Also, copolymer, therapeutic agent, and mode of immobilization or incorporation will be selected to ensure that the release of the agent occurs in a controlled fashion.

In still other embodiments, the invention provides copolymers which are useful as biosensors. In Example 2, the immobilization of redox-active molecules in a sulfonated multiblock copolymer is demonstrated. A copolymer incorporating a redox-active molecule is useful as a biosensor where electrical communication between an electrode and a redox-active enzyme cofactor is important.

It will also be appreciated that the above aspects of the invention can be combined. For example, a cardiovascular implant can be coated with a sulfonated copolymer which incorporates a therapeutic drug (for example, an antiinflammatory drug). Such an implant would combine antithrombogenicity with the ability to improve endothelial cell growth on the implant surface, while releasing an antiinflammatory drug to speed the healing process. Another example of a combination is an implant which features an immobilized TGF-β superfamily factor (e.g., bone morphogenic protein (BMP)) in the sulfonated copolymer. Such an implant would act to stimulate the growth and morphogenesis of bone on the implant surface through the additive effect of the natural growth factor derivative of demineralized bone and the bone-matrix stimulating effect of the sulfonated copolymer.

The mechanical strength or other qualities of the sulfonated multiblock copolymers of the invention is at least partly dependent on the degree of sulfonation of the copolymer, and can be adjusted by the inclusion of additives. For example, the addition of polyterpenes increases the stiffness or rigidity of the copolymer. Addition of multivalent cations, such as multivalent metal ions (e.g., $Al^{3+}$, $Zn^{2+}$, and the like) or organic cations or polycations, such as polylysine, also increases the stiffness of the copolymer. Other methods of stiffening the subject sulfonated copolymers include radiation cross-linking, for example with gamma rays or high-energy electrons. A stiffer copolymer can be desirable for those applications which require such stiffness for the production of the desired article, that is, where working of the article is more readily accomplished on a rigid workpiece. Furthermore, addition of appropriate additives can increase the mechanical strength of the copolymer sufficiently to permit the use of the copolymer to form a finished article without an underlying substrate. For example, a heart valve must be rigid and strong to function efficiently and to prevent failure when implanted; thus, a strong, rigid copolymer is necessary, and may be obtained by appropriate choice of additives. The skilled artisan will be able to determine additives appropriate for imparting desired qualities to the copolymers of the invention.

The subject copolymers also exhibit electromechanical properties; that is, application of a weak electric field causes the copolymer to move, bend, or deform in response to the field. This property is useful for providing implantable devices which can be modified in situ by application of an electric field, thus providing an implant which can be customized, adapted, or modified after implantation without removing the implant and without need for surgical intervention.

Other properties of the subject sulfonated copolymers useful in the present invention can also be optimized for particular applications. For example, the degree of sulfonation of the copolymer determines, at least in part, the relative hydrophobicity of the copolymer, and the charge density on the copolymer surface. That is, the greater the extent of sulfonation of the copolymer, the more hydrophilic the copolymer will be, and the more anionic groups will be present on the copolymer surface. The extent of sulfonation can thus determine properties such as the ability to interact with (e.g., retain on the surface or within the copolymer matrix) various molecules such as drugs, as well as determining cell affinity for the copolymer surface. In preferred embodiments, the copolymer is at least 20%, 30%, 50%, 70%, or 90% sulfonated.

EXEMPLIFICATION

Example 1

The antithrombogenic properties of the sulfonated multiblock copolymers of the invention were demonstrated in an in vitro system. Wells of a standard six-well tissue culture dish were coated with sulfonated styrene-ethylene/butylene-styrene triblock copolymers of the invention according to standard techniques. The copolymers differed in the extent of sulfonation; both 30% and 74% sulfonated copolymers were tested. Control wells were not coated with a copolymer; however, the control wells had an anionic (carboxylated) surface as a result of the standard manufacturing process. A glass tube was used as an uncharged control surface.

To each well (and the glass tube) was added freshly drawn human blood. The time required for the blood in each well (or tube) to clot was measured; the wells were stirred periodically to determine fibrin and clot formation. The results are shown in the Table:

TABLE

| Treatment | Time (in munutes) | | | | | | | | | | | | |
|---|---|---|---|---|---|---|---|---|---|---|---|---|---|
| | 0 | 8 | 10 | 15 | 20 | 25 | 30 | 35 | 40 | 45 | 55 | 65 | 75 |
| anionic (uncoated well) | NC | NC | NC | F | C | C | C | C | C | C | C | C | C |
| glass tube | NC | C | C | C | C | C | C | C | C | C | C | C | C |
| 30% sulfonation | NC | NC | NC | NC | NC | F | small clot | C | C | C | C | C | C |
| 74% sulfonation | NC | NC | NC | NC | NC | NC | NC | NC | NC | NC | NC | NC | C |

NC = No clot formed
F = Fibrin appears
C = Clot formed

It can be seen from the Table that sulfonated styrene-ethylene-butylene-styrene block copolymer significantly retards fibrin formation and clotting. The more highly sulfonated copolymer shows greater antithrombogenic activity than the less sulfonated copolymer; both copolymers retard clotting more than the anionic control well or the untreated control surface.

Example 2

The ability of the sulfonated styrene-ethylene-butylene-styrene block copolymers of the invention to immobilize molecules of interest was demonstrated in the following in this experiment.

The redox-active molecules shown in FIG. 1A were immobilized in the sulfonated triblock copolymer of styrene-ethylene/butylene-styrene. The copolymers thus formed were examined by cyclic voltammetry to determine whether the added molecules were incorporated and remained redox-active. In each case, the molecules were shown to be active by cyclic voltammetry.

Figure 1B:
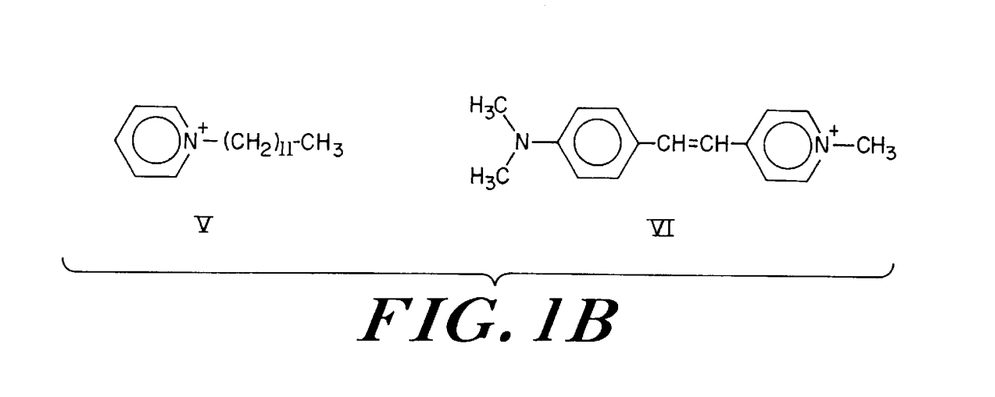

The compounds shown in FIG. 1B were also shown to be incorporated by the sulfonated triblock copolymer of styrene-ethylene/butylene-styrene.

Example 3

Figure 2:
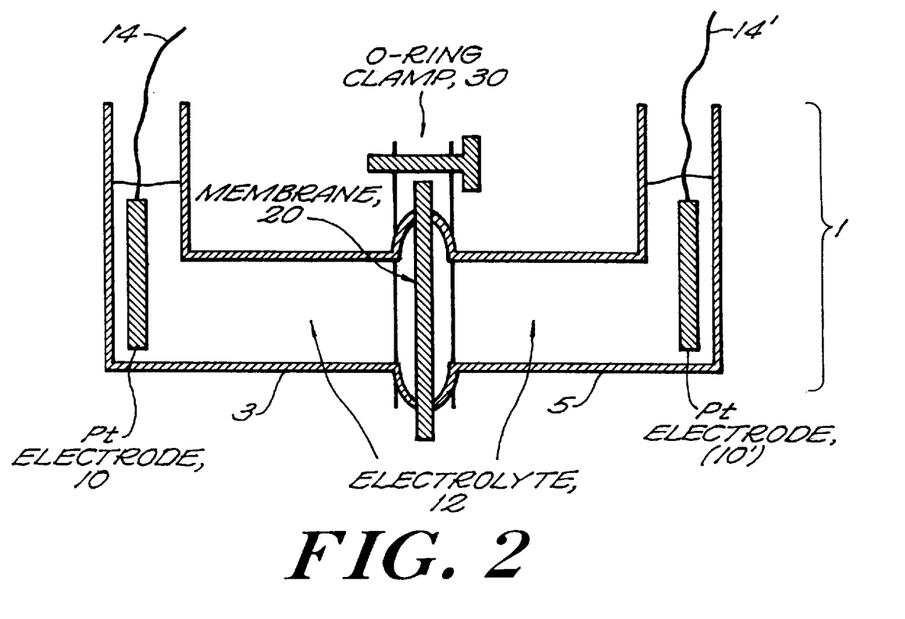
FIG. 2 depicts a cell which allows for the measurement of ionic conductivity through a membrane.

FIG. 2 depicts a cell which allows for the measurement of ionic conductivity through a membrane including various molecules. The cell 1 includes cathode side 3 and anode side 5, each side having an electrode (10, 10'), e.g., a platinum electrode, and the two sides 3, 5 being separated from each other by a membrane (20) of a material to be tested. The electrodes 10, 10' are connected to a source of electric current (not shown) through leads 14, 14'. Each half 3, 5 of the cell 1 is filled with an electrolyte solution (12), and the cell is supported by a clamp (30). The following observations were made with this cell: a) The compound trimethylaminomethylferrocene, which was ion-exchanged into block copolymer film (styrene-ethylene/butylene-styrene, about 50% sulfonated), was released from the polymer when a field of about 10 V/cm was applied. It was released into the cathode (−) side of the cell, as evidenced by the appearance of a yellow color on the cathode side. This result may reflect electrophoretic movement of the cationic ferrocene compound toward the cathode, or it might be due to a change in the S-PS phase of the polymer, which may expand due to the applied field, facilitating release. b) When the membrane 20 described above contains trimethylaminomethyl-ferrocene, the membrane still allows ions to pass; however, a membrane containing the more hydrophobic dimethylheptylaminomethylferrocene appears to have lower ionic conductivity. This observation suggests that the S-PS lamellae have been lined or modified with hydrophobic molecules, leading to a hydrophobic environment that slows or prevents movement of aqueous salt ions through the membrane, and consequent low conductivity. This suggests that a "modifier cation," as described above, could be useful in controlling the permeability of the membrane and hence the rate at which drugs are released through the membrane. Moreover, it suggests that ionic conductivity can be increased by oxidizing ferrocene to the ferrocenium cation, which would increase the hydrophilicity and increase the ionic conductivity. Since this redox process is reversible, membrane permeability to aqueous solutions can be controlled simply by application of appropriate electric potential to the membrane, creating an intelligent membrane which acts as a gate for controlled drug delivery.

Example 4

The ability of endothelial cells to attach, grow, and express a differentiated phenotype was demonstrated in an in vitro system. In this experiment, standard 24-well tissue culture plates were utilized. Enough wells in each plate to provide six replicates of each condition were coated with 150 microliters of solutions of the sulfonated copolymer of the invention at each of three different sulfonation levels. After polymer treatment, the wells were rinsed with sterile distilled water for thirty minutes, followed by three rinses with Hank's Balance Salt Solution. Controls consisted of wells of normal culture ware (that is, culture ware that is treated to allow cell adhesion and cell growth, by carboxylation of the surface, thereby rendering the surface anionic) that were coated with the subject sulfonated styrene-ethylene/butylene-styrene copolymer, and, as a negative control, culture dishes obtained from the manufacturer that had not been treated to promote adhesion and growth of cells (untreated controls). Into each of these wells were introduced 100,000 porcine aortic endothelial cells in 1 ml of M199 medium (Sigma Chemical Co., St. Louis, Mo.) with 10% fetal bovine serum (FBS), leaving at least two wells per condition inoculated just with medium to serve as a blank. Plates were then placed in an incubator at 37° C., with an atmosphere containing 5% $CO_2$, for 48 hours. After the incubation period the medium was removed from each well, spun down in a centrifuge, and frozen separately to use in the phenotype expression assays. 500 ml of medium were added back to each well to allow a cell proliferation assay (CellTiter AQueous, Promega, Inc., Madison, Wiss.) to be performed.

Figure 3:
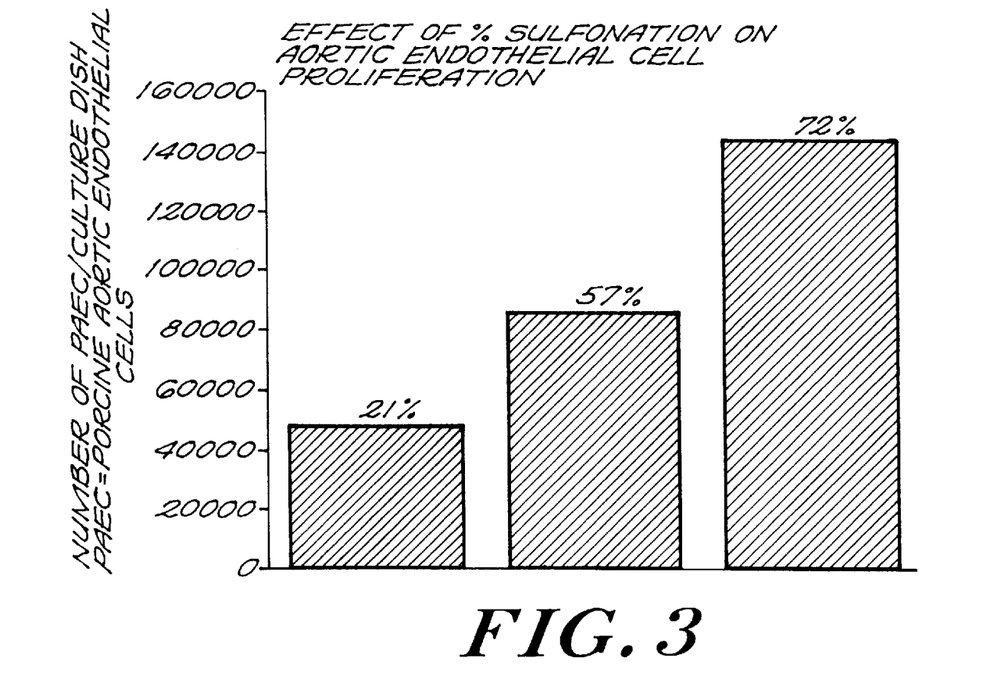
FIG. 3 is a bar graph representing the effect of varying percentages of sulfonation on cell adhesion to selected copolymers of the invention.
Figure 4:
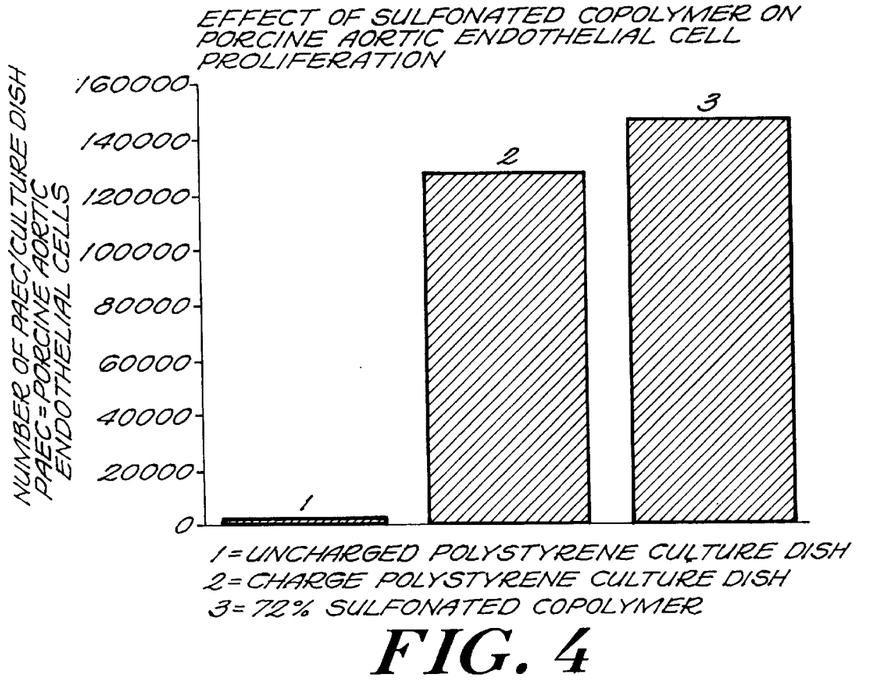
FIG. 4 is a bar graph depicting the amount of cell adhesion on several surfaces.

Microscopic examination demonstrated that aortic endothelial cells become attached to surfaces, such as microtiter wells, treated with the subject copolymer, and have the appearance of normal cells. In contrast, untreated control wells do not promote endothelial cell attachment. FIGS. 3 and 4 are graphs showing the results of the cell proliferation assay. As indicated in FIG. 3, the proliferation of cells on the sulfonated polymer is related to the degree of sulfonation in the polymer (21%, 57% or 72%; greater sulfonation of the polymer increases cell proliferation), and FIG. 4 indicates that the proliferation of aortic endothelial cells at the highest percentage sulfonation utilized compares favorably to the commercially-available anionically charged polystyrene culture dish, which is designed to promote cell adhesion and growth (first column: uncharged polystyrene culture dish; second column: commercially-available anionic polystyrene culture dish; third column: 72% sulfonated styrene-ethylene/butylene-styrene block copolymer-treated culture dish).

Figure 5:
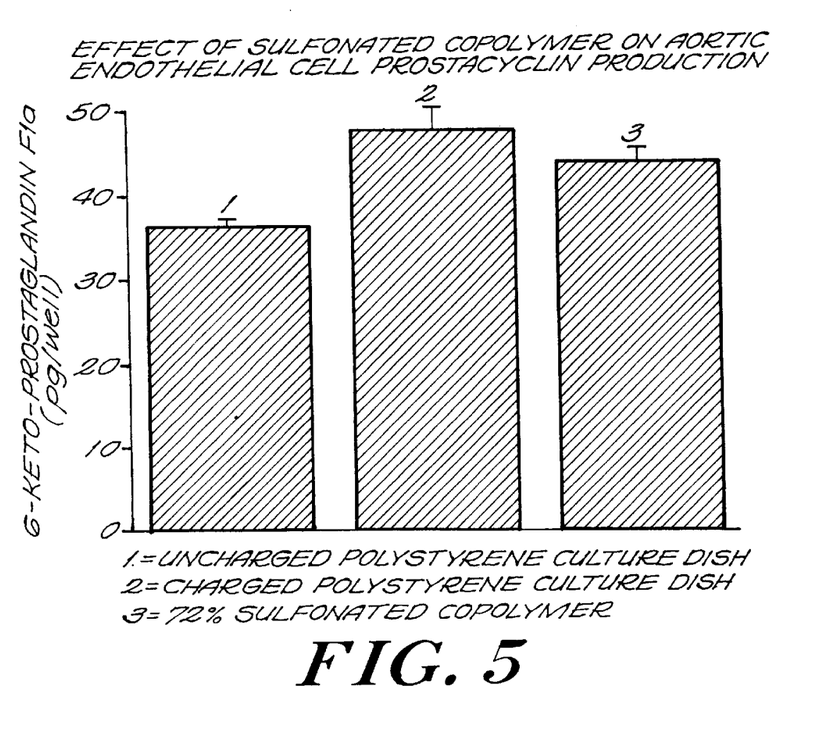
FIG. 5 is a bar graph showing aortic endothelial cell prostacyclin production on several surfaces.

FIG. 5 shows the results of a phenotypic expression assay on the incubation media of the experimental and control conditions described above. The assay utilized was the Biotrak 6-keto-prostaglandin F 1a EIA. The compound 6-keto-prostaglandin is normally produced by endothelial cells, but is not produced if the endothelial cells dedifferentiate. As can be seen from FIG. 5, the cells seeded on the sulfonated copolymer all continued to express the endothelial phenotype, and did not appear to dedifferentiate (first column: uncharged polystyrene culture dish; second column: commercially-available anionic polystyrene culture dish; third column: 72% sulfonated styrene-ethylene/butylene-styrene block copolymer-treated culture dish).

These experiments illustrate the efficacy of the sulfonated copolymers of the invention in normal cell growth and adhesion where endothelialization is a desirable feature of the material.

Example 5

A piece of Teflon sheet (Xytex, Norton Co.) with 10 micron pore structure was dipped in an approximately 3% (w/w) solution of the sulfonated styrene-ethylene-butylene-styrene block copolymer (about 50% sulfonated), shaken to remove liquid droplets, and dried for several hours. The treated material was noticeably different to the touch compared to the untreated Teflon sheet. The wettability of the treated sheet was also altered compared to an untreated control: water beaded on the untreated porous Teflon, but wetted (and was absorbed into) the Teflon-sulfonated copolymer hybrid. The hybrid material retains the strength and resilience of porous Teflon, but acquires characteristics of the sulfonated polymer (e.g., a non-thrombogenic surface, ability to grow and develop viable and healthy tissues on the surface, and ability to immobilize or deliver biologically important substances). Where infiltration of the sulfonated copolymer phase into a second material is slow, as where the second material has small pores, the copolymer can be driven into the porous structure electrophoretically.

The contents of all references and patents cited herein are hereby incorporated by reference.

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A nonthrombogenic article for use in contact with blood or blood products, the ariicle comprising a substrate hanving at least one surface, said surface having disposed thereon an anionic sulfonated multiblock copolymer, wherein said multiblock copolymer is at least 20% sulfonated.

2. A nonthrombogenic article for use in contact with blood or blood products, the article comprising a substrate having at least one surface, said surface having disposed thereon an anionic sulfonated styrene-ethylene/butylene-styrene triblock copolymer, wherein said triblock copolymer is at least 20% sulfonated.

3. The article of claim 2, wherein said triblock copolymer is coated on said substrate.

4. The article of claim 2, wherein said triblock copolymer is at least 35% sulfonated.

5. The article of claim 2, wherein said triblock copolymer entraps a drug.

6. The article of claim 2, wherein said triblock copolymer is grafted to said substrate.

7. The article of claim 2, wherein said article comprises a material selected from the group consisting of polytetrafluoroethylene, polyethylene tetraphthalate, titanium oxide, magnetic particles, and calcium phosphate.

8. The article of claim 2, wherein the article is selected from the group consisting of stents, catheters, cannulae, tubing, vascular grafts, artificial hearts, hear valves, pacemakers, implants, artificial joints, and prostheses.

9. The aricle of claim 2, wherein the article is an electrical lead.

10. A method of manufacturing a thromboresistant article for use in contact with blood or blood products, the method comprising coaling at least one surface of an article with an anionic sulfonated multiblock copolymer, wherein said multiblock copolymer is at least 20% sulfonated.

11. The method of claim 10, wherein the multiblock copolymer is a sulfonated styrene-ethylene/butylene-styrene triblock copolymer.

12. The method of claim 11, wherein said triblock copolymer is at least 35% sulfonated.

13. The method of claim 11, wherein said triblock copolymer entraps a drug.

14. The method of claim 11, wherein the aricle comprises a material selected from the group consisting of polytetrafluoroethylene, polyethylene teraphtalate, titanium oxide, magnetic paticles, and calcium phosphate.

15. The method of claim 11, wherein the article is selected from the group consisting of stents, catheters, cannulae, tubing, vascular grafts, artificial hearts, heart valves, pacemakers, implants, artificial joints, and prostheses.

16. The method of claim 11, wherein the article is an electrical lead.

17. A medical implant which can be modified in situ by application of an electric field, the implant comprising a substrate having disposed thereon an anionic sulfonated multiblock copolymer, wherein said multiblock copolymer is at least 20% sulfonated.

18. The medical implant of claim 17, wherein the multiblock copolymer is a sulfonated styrene-ethylene/butylene-styrene triblock copolymer.

19. The medical implant of claim 18, wherein the triblock copolymer entraps a drug.

* * * * *